(12) United States Patent
Takai et al.

(10) Patent No.: US 6,180,760 B1
(45) Date of Patent: Jan. 30, 2001

(54) ACTIN FILAMENT-BINDING PROTEIN "L-AFADIN"

(75) Inventors: Yoshimi Takai; Hiroyuki Nakanishi, both of Hyogo; Kenji Mandai, Osaka-fu; Manabu Wada; Hiroshi Obaishi, both of Hyogo, all of (JP)

(73) Assignees: Japan Science and Technology Corp., Saitama; Manabu Wada; Hiroshi Obaishi, both of Hyogo, all of (JP)

( * ) Notice: Under 35 U.S.C. 154(b), the term of this patent shall be extended for 0 days.

(21) Appl. No.: 09/157,420

(22) Filed: Sep. 21, 1998

(30) Foreign Application Priority Data

Sep. 22, 1997 (JP) .................................................. 9-257043

(51) Int. Cl.[7] .............................. C07K 1/00; C07K 16/09; C07H 21/02
(52) U.S. Cl. ........................ 530/350; 536/23.1; 530/387.1
(58) Field of Search ................................ 530/350, 387.1; 536/23.1

(56) References Cited

U.S. PATENT DOCUMENTS 5,200,313 * 4/1993 Carrico ...................................... 435/6

FOREIGN PATENT DOCUMENTS

94/26930 * 11/1994 (WO) .

OTHER PUBLICATIONS

Mandai et al. Afadin: A novel actin filament–binding protein with one PDZ domain localized at cadherin–based cell–to–cell adherens. J. Cell Biol. 139(2):517–528, Oct. 1997.*
Canaani et al. Accessin No. Q75179 from the N_Geneseq_34 database, Aug. 1995.*

* cited by examiner

*Primary Examiner*—Karen Cochrane Carlson
*Assistant Examiner*—Devesh Srivastava
(74) *Attorney, Agent, or Firm*—Wenderoth, Lind & Ponack, L.L.P.

(57) ABSTRACT

An actin filament-binding protein 1-Afadin having the amino acid sequence of SEQ ID NO: 1 or having an amino acid sequence substantially the same as that of SEQ ID NO: 1, a cDNA sequence encoding the protein, a genomic DNA sequence to which the cDNA sequence or a partial sequence thereof is hybridized, and an antibody specifically recognizing 1-Afadin are provided. The protein is a novel actin filament-binding protein localized at the cadherin based cell-to-cell adherens junction and the other products are useful as the genetic materials for industrially utilizing the protein.

4 Claims, 9 Drawing Sheets

(2 of 9 Drawing Sheet(s) Filed in Color)

SEQUENCE LISTING

```
<160> NUMBER OF SEQ ID NOS: 1

<210> SEQ ID NO 1
<211> LENGTH: 1829
<212> TYPE: PRT
<213> ORGANISM: rat

<400> SEQUENCE: 1

Met Ser Ala Gly Gly Arg Asp Glu Glu Arg Arg Lys Leu Ala Asp Ile
 1               5                   10                  15

Ile His His Trp Asn Ala Asn Arg Leu Asp Leu Phe Glu Ile Ser Gln
             20                  25                  30

Pro Thr Glu Asp Leu Glu Phe His Gly Val Met Arg Phe Tyr Phe Gln
         35                  40                  45

Asp Lys Ala Ala Gly Asn Phe Ala Thr Lys Cys Ile Arg Val Ser Ser
     50                  55                  60

Thr Ala Thr Thr Gln Asp Val Ile Glu Thr Leu Ala Glu Lys Phe Arg
 65                  70                  75                  80

Pro Asp Met Arg Met Leu Ser Ser Pro Lys Tyr Ser Leu Tyr Glu Val
```

-continued

```
                      85                       90                        95
His Val Ser Gly Glu Arg Arg Leu Asp Ile Asp Glu Lys Pro Leu Val
                100                 105                 110

Val Gln Leu Asn Trp Asn Lys Asp Asp Arg Glu Gly Arg Phe Val Leu
            115                 120                 125

Lys Asn Glu Asn Asp Ala Ile Pro Ala Lys Lys Ala Gln Ser Asn Gly
        130                 135                 140

Pro Glu Lys Gln Glu Lys Glu Gly Val Ile Gln Asn Phe Lys Arg Thr
145                 150                 155                 160

Leu Ser Lys Lys Glu Lys Lys Glu Lys Lys Arg Glu Lys Glu Ala
                165                 170                 175

Leu Arg Gln Ala Ser Asp Lys Glu Glu Arg Pro Ser Gln Gly Asp Asp
            180                 185                 190

Ser Glu Asn Ser Arg Leu Ala Ala Glu Val Tyr Lys Asp Met Pro Glu
        195                 200                 205

Thr Ser Phe Thr Arg Thr Ile Ser Asn Pro Glu Val Met Lys Arg
        210                 215                 220

Arg Arg Gln Gln Lys Leu Glu Lys Arg Met Gln Glu Phe Arg Ser Ser
225                 230                 235                 240

Asp Gly Arg Pro Asp Ser Gly Gly Thr Leu Arg Ile Tyr Ala Asp Ser
                245                 250                 255

Leu Lys Pro Asn Ile Pro Tyr Lys Thr Ile Leu Leu Ser Thr Thr Asp
            260                 265                 270

Pro Ala Asp Phe Ala Val Ala Glu Ser Leu Glu Lys Tyr Gly Leu Glu
        275                 280                 285

Lys Glu Asn Pro Lys Asp Tyr Cys Ile Ala Arg Val Met Leu Pro Pro
290                 295                 300

Gly Ala Gln His Ser Asp Glu Arg Gly Ala Lys Glu Ile Ile Leu Asp
305                 310                 315                 320

Asp Asp Glu Cys Pro Leu Gln Ile Phe Arg Glu Trp Pro Ser Asp Lys
                325                 330                 335

Gly Ile Leu Val Phe Gln Leu Lys Arg Arg Pro Pro Asp Tyr Ile Pro
            340                 345                 350

Lys Lys Met Lys Lys His Val Glu Gly Lys Pro Leu Lys Gly Lys Asp
        355                 360                 365

Arg Ala Asp Gly Ser Gly Tyr Gly Ser Ala Leu Pro Pro Glu Lys Leu
370                 375                 380

Pro Tyr Leu Val Glu Leu Ser Pro Gly Arg Arg Asn His Phe Ala Tyr
385                 390                 395                 400

Tyr Ser Tyr His Thr Tyr Glu Asp Gly Ser Asp Ser Arg Asp Lys Pro
                405                 410                 415

Lys Leu Tyr Arg Leu Gln Leu Ser Val Thr Glu Val Gly Thr Glu Lys
            420                 425                 430

Phe Asp Asp Asn Ser Ile Gln Leu Phe Gly Pro Gly Ile Gln Pro His
        435                 440                 445

His Cys Asp Leu Thr Asn Met Asp Gly Val Val Thr Val Thr Pro Arg
        450                 455                 460

Ser Met Asp Ala Glu Thr Tyr Val Asp Gly Gln Arg Ile Ser Glu Thr
465                 470                 475                 480

Thr Met Leu Gln Ser Gly Met Arg Leu Gln Phe Gly Thr Ser His Val
                485                 490                 495

Phe Lys Phe Val Asp Pro Ile Gln Asp His Val Leu Ser Lys Arg Ser
            500                 505                 510
```

-continued

```
Val Asp Gly Gly Leu Met Val Lys Gly Pro Arg His Lys Pro Gly Ala
        515                 520                 525
Val Gln Glu Thr Thr Phe Glu Leu Gly Gly Asp Ile His Ser Gly Thr
        530                 535                 540
Ala Leu Pro Ala Ser Arg Ser Thr Thr Arg Leu Asp Ser Asp Arg Val
545                 550                 555                 560
Ser Ser Ala Ser Ser Thr Ala Glu Arg Gly Met Val Lys Pro Met Ile
                565                 570                 575
Arg Leu Asp Gln Glu Gln Asp Tyr Arg Arg Glu Ser Arg Thr Gln
            580                 585                 590
Asp Ala Ala Gly Pro Glu Leu Met Leu Pro Ala Ser Ile Glu Phe Arg
            595                 600                 605
Glu Ser Ser Glu Asp Ser Phe Leu Ser Ala Ile Ile Asn Tyr Thr Asn
            610                 615                 620
Ser Ser Thr Val His Phe Lys Leu Ser Pro Thr Tyr Val Leu Tyr Met
625                 630                 635                 640
Ala Cys Arg Tyr Val Leu Ser Ser Gln His Arg Pro Asp Ile Ser Pro
                645                 650                 655
Thr Glu Arg Thr His Lys Ala Ile Ala Val Val Asn Lys Met Val Ser
                660                 665                 670
Met Met Glu Gly Val Ile Gln Glu Val Asp Gln Val Asp Gln Lys Gln
        675                 680                 685
Lys Asn Ile Ala Gly Ala Leu Ala Phe Trp Met Ala Asn Ala Ser Glu
        690                 695                 700
Leu Leu Asn Phe Ile Lys Gln Asp Arg Asp Leu Ser Arg Ile Thr Leu
705                 710                 715                 720
Asp Ala Gln Asp Val Leu Ala His Leu Val Gln Met Ala Phe Lys Tyr
                725                 730                 735
Leu Val His Cys Leu Gln Ser Glu Leu Asn Asn Tyr Met Pro Ala Phe
                740                 745                 750
Leu Asp Asp Pro Glu Glu Asn Ser Leu Gln Arg Pro Lys Ile Asp Asp
                755                 760                 765
Val Leu His Thr Leu Thr Gly Ala Met Ser Leu Leu Arg Arg Cys Arg
770                 775                 780
Val Asn Ala Ala Leu Thr Ile Gln Leu Phe Ser Gln Leu Phe His Phe
785                 790                 795                 800
Ile Asn Met Trp Leu Phe Asn Arg Leu Val Thr Asp Pro Asp Ser Gly
                805                 810                 815
Leu Cys Ser His Tyr Trp Gly Ala Ile Ile Arg Gln Gln Leu Gly His
                820                 825                 830
Ile Glu Ala Trp Ala Glu Lys Gln Gly Leu Glu Leu Ala Ala Asp Cys
            835                 840                 845
His Leu Ser Arg Ile Val Gln Ala Thr Thr Leu Leu Thr Met Asp Lys
            850                 855                 860
Tyr Val Pro Asp Asp Ile Pro Asn Ile Asn Ser Thr Cys Phe Lys Leu
865                 870                 875                 880
Asn Ser Leu Gln Leu Gln Ala Leu Leu Gln Asn Tyr His Cys Ala Pro
                885                 890                 895
Asp Glu Pro Phe Ile Pro Thr Asp Leu Ile Glu Asn Val Val Ala Val
                900                 905                 910
Ala Glu Asn Thr Ala Asp Glu Leu Ala Arg Ser Asp Gly Arg Asp Val
            915                 920                 925
```

-continued

```
Gln Leu Glu Glu Asp Pro Asp Leu Gln Leu Pro Phe Leu Leu Pro Glu
    930                 935                 940

Asp Gly Tyr Ser Cys Asp Val Val Arg Asn Ile Pro Asn Gly Leu Gln
945                 950                 955                 960

Glu Phe Leu Asp Pro Leu Cys Gln Arg Gly Phe Cys Arg Leu Val Pro
                965                 970                 975

His Thr Arg Ser Pro Gly Thr Trp Thr Ile Tyr Phe Glu Gly Ala Asp
            980                 985                 990

Tyr Glu Ser His Leu Met Arg Glu Asn Thr Glu Leu Thr Gln Pro Leu
        995                 1000                1005

Arg Lys Glu Pro Glu Val Ile Thr Val Thr Leu Lys Lys Gln Asn Gly
    1010                1015                1020

Met Gly Leu Ser Ile Val Ala Ala Lys Gly Ala Gly Gln Asp Lys Leu
1025                1030                1035                1040

Gly Ile Tyr Val Lys Ser Val Val Lys Gly Gly Ala Ala Asp Val Asp
                1045                1050                1055

Gly Arg Leu Ala Ala Gly Asp Gln Leu Leu Ser Val Asp Gly Arg Ser
            1060                1065                1070

Leu Val Gly Leu Ser Gln Glu Arg Ala Ala Glu Leu Met Thr Arg Thr
        1075                1080                1085

Ser Ser Val Val Thr Leu Glu Val Ala Lys Gln Gly Ala Ile Tyr His
    1090                1095                1100

Gly Leu Ala Thr Leu Leu Asn Gln Pro Ser Pro Met Met Gln Arg Ile
1105                1110                1115                1120

Ser Asp Arg Arg Gly Ser Gly Lys Pro Arg Pro Lys Ser Glu Gly Phe
                1125                1130                1135

Glu Leu Tyr Asn Asn Ser Ala Gln Asn Gly Ser Pro Glu Ser Pro Gln
            1140                1145                1150

Met Pro Trp Thr Glu Tyr Ser Glu Pro Lys Lys Leu Pro Gly Asp Asp
        1155                1160                1165

Arg Leu Met Lys Asn Arg Ala Asp His Arg Ser Ser Pro Asn Val Ala
    1170                1175                1180

Asn Gln Pro Pro Ser Pro Gly Gly Lys Ser Pro Tyr Thr Ser Gly Thr
1185                1190                1195                1200

Ala Ala Lys Ile Thr Ser Val Ser Thr Gly Asn Leu Cys Thr Glu Glu
            1205                1210                1215

Gln Thr Pro Pro Pro Arg Pro Glu Ala Tyr Pro Ile Pro Thr Gln Thr
        1220                1225                1230

Tyr Thr Arg Glu Tyr Phe Thr Phe Pro Ala Ser Lys Ser Gln Asp Arg
    1235                1240                1245

Met Ala Pro Val Gln Asn Gln Trp Pro Asn Tyr Glu Glu Lys Pro His
1250                1255                1260

Met His Thr Glu Ser Asp His Ala Ser Ile Ala Ile Gln Arg Val Thr
            1265                1270                1275                1280

Arg Ser Gln Glu Glu Leu Arg Glu Glu Lys Val Tyr Gln Leu Glu Arg
        1285                1290                1295

His Arg Val Glu Ser Gly Met Asp Arg Lys Cys Asp Ser Asp Met Trp
    1300                1305                1310

Ile Asn Gln Ser Ser Ser Val Glu Ser Ser Thr Ser Ser Gln Glu His
        1315                1320                1325

Leu Asn His Ser Ser Lys Ser Val Thr Pro Ala Ser Thr Leu Thr Lys
    1330                1335                1340

Ser Gly Pro Gly Arg Trp Lys Thr Pro Ala Ala Val Leu Pro Thr Pro
```

```
                1345                1350                1355                1360

Val Ala Val Ser Gln Pro Ile Arg Thr Asp Leu Pro Pro Pro Pro
                1365                1370                1375

Pro Pro Pro Ala His Tyr Thr Ser Asp Phe Asp Gly Ile Ser Met Asp
        1380                1385                1390

Leu Pro Leu Pro Pro Pro Ala Asn Gln Ala Ala Pro Gln Ser Ala
        1395                1400                1405

Gln Val Ala Ala Ala Glu Arg Lys Lys Arg Glu Glu His Gln Arg Trp
        1410                1415                1420

Tyr Glu Lys Glu Lys Ala Arg Leu Glu Glu Arg Glu Arg Lys Arg
1425                1430                1435                1440

Arg Glu Gln Glu Arg Lys Leu Gly Gln Met Arg Thr Gln Ser Leu Asn
                1445                1450                1455

Pro Ala Ser Phe Ser Pro Leu Ala Thr Gln Ala Lys Pro Glu Lys Pro
        1460                1465                1470

Ser Thr Leu Gln Arg Pro Gln Glu Thr Val Ile Arg Glu Leu Gln Pro
        1475                1480                1485

Gln Gln Gln Pro Arg Thr Ile Glu Arg Arg Asp Leu Gln Tyr Ile Thr
        1490                1495                1500

Ile Ser Lys Glu Glu Leu Ser Ser Gly Asp Ser Leu Ser Pro Asp Pro
1505                1510                1515                1520

Trp Lys Arg Asp Ala Arg Glu Lys Leu Glu Lys Gln Gln Gln Met His
        1525                1530                1535

Ile Val Asp Met Leu Ser Lys Glu Ile His Glu Leu Gln Asn Lys Gly
            1540                1545                1550

Asp Arg Thr Ala Glu Glu Ser Asp Arg Leu Arg Lys Leu Met Leu Glu
        1555                1560                1565

Trp Gln Phe Gln Lys Arg Leu Gln Glu Ser Lys Gln Lys Asp Glu Asp
        1570                1575                1580

Asp Asp Glu Glu Glu Asp Asp Asp Val Asp Thr Met Leu Ile Met Gln
1585                1590                1595                1600

Arg Leu Glu Ala Glu Arg Arg Ala Arg Leu Gln Asp Glu Glu Arg Arg
                1605                1610                1615

Arg Gln Gln Gln Leu Glu Glu Met Arg Lys Arg Glu Val Glu Asp Arg
        1620                1625                1630

Val Arg Gln Glu Glu Asp Gly Arg His Gln Glu Glu Glu Arg Val Lys
        1635                1640                1645

Arg Asp Ala Glu Glu Lys Arg Arg Gln Glu Glu Gly Tyr Tyr Ser Arg
        1650                1655                1660

Leu Glu Ala Glu Arg Arg Arg Gln His Glu Glu Ala Ala Arg Arg Leu
1665                1670                1675                1680

Leu Glu Pro Glu Glu Pro Gly Leu Ser Arg Pro Pro Leu Pro Gln Asp
            1685                1690                1695

Tyr Glu Pro Pro Ser Gln Ser Ser Ala Pro Ser Ala Pro Pro Pro
        1700                1705                1710

Pro Gln Arg Asn Ala Ser Tyr Leu Lys Thr Gln Val Leu Ser Pro Asp
```

-continued

```
            1715                1720                1725
Ser Leu Phe Thr Ala Lys Phe Val Ala Tyr Asp Asp Asp Glu Glu
            1730                1735                1740
Glu Asn Tyr Val Pro Ala Gly Pro Asn Ser Tyr Ser Gly Ser Ala Gly
1745                1750                1755                1760
Thr Thr Ala Gly Thr Tyr Asp Ala Pro Arg Asp Thr Arg Glu Lys Leu
                1765                1770                1775
Ser Arg Ser Gln Asp Ala Asp Leu Pro Gly Ser Ser Gly Ala Pro Glu
            1780                1785                1790
Asn Leu Thr Phe Arg Glu Arg Gln Arg Leu Phe Ser Gln Gly Gln Asp
            1795                1800                1805
Val Ser Asp Lys Val Lys Ala Ser Arg Lys Leu Thr Glu Leu Glu Asn
    1810                1815                1820
Glu Leu Asn Thr Lys
1825
```

ACTIN FILAMENT-BINDING PROTEIN "L-AFADIN"

BACKGROUND OF THE INVENTION

1. Field of the Invention

The present invention relates to a novel actin filament-binding protein "1-Afadin". More precisely, the present invention relates to a novel animal protein 1-Afadin that contributes to the cell-to-cell adherens junction (AJ) having an important role in individual formation of animals and pathigenesis.

2. Description of the Related Art

In various cellular events, such as cell adhesion, cell motility, and cell shape determination, specialized membrane domains are formed with transmembrane proteins, such as cell adhesion molecules, receptors, and channels, and these domains are often associated with the actin cytoskeleton (Biochem. Biophys, Acta 737:305–341, 1983; Curr. Opin. Cell Biol. 1:103–109, 1989; Cell Motil. Cytoskeleton 20:1–6, 1991; Curr. Opin. Cell Biol. 3:849–853, 1991; Science 258:955–964, 1992; Curr. Opin. Cell Biol. 4:834–839, 1992; Curr. Opin. Cell Biol. 5:653–660, 1993; Trends Biochem. Sci. 22:53–58, 1997). The linkage between the actin cytoskeleton and the plasma membrane plays a crucial role in these cellular events, and proteins linking the actin cytoskeleton to the transmembrane proteins have been identified. However, the molecular basis of the linkage between the actin cytoskeleton and the plasma membrane is not fully understood.

To understand this molecular linkage, the cell adhesion sites have been most extensively studied (Biochem. Biophys. Acta 737:305–341, 1983; Curr. Opin. Cell Biol. 1:103–109, 1989; Cell Motil. Cytoskeleton 20:1–6, 1991; Curr. Opin. Cell Biol. 3:849–853, 1991; Science 258:955–964, 1992; Curr. Opin. Cell Biol. 4:834–839, 1992; Curr. Opin. Cell Biol. 5:653–660, 1993; Trends Biochem. Sci. 22:53–58, 1997). As a result, the actin filament (F-actin)-associated cell adhesion sites are subclassed into two types: cell-to-cell and cell-to-matrix adherens junctions. Many linker proteins have been identified at the cell-to-cell AJ where cadherin interacts with each other at the extracellular surface (Development 102:639–655, 1988; Cell Motil. Cytoskeleton 20:1–6, 1991; Science 251:1451–1455, 1991; Curr. Opin. Cell Biol. 4:834–839, 1992; EMBO J. 8:1711–1717, 1989; Cell 65:849–857, 1991; Science 251:1451–1455, 1991; Curr. Opin. Cell Biol. 4:834–839, 1992). Among these binding proteins, α-catenin directly interacts with F-actin (Proc. Natl. Acad. Sci. U.S.A. 92, 8813–8817, 1995). α-Catenin also indirectly interacts with F-actin through α-actinin and/or ZO-1 (J. Cell. Biol. 130:67–77, 1995; J. Cell. Biol. 138:181–192, 1997). Further, Vinculin, another F-actin-binding protein, is concentrated at the cell-to-cell AJ, although its interacting molecules at cell-to-cell AJ have not yet been identified (Cell Motil. Cytoskeleton 20:1–6, 1991; Curr. Opin. Cell Biol. 4:834–839, 1992). At cell-to-matrix AJ where integrin interacts with matrix proteins at the extracellular surface, the cytoplasmic domain directly or indirectly interacts with F-actin-binding proteins, including α-actinin, vinculin, and talin (Ann. Rev. cell Dev. Biol. 11: 379–416, 1995).

As described above, many F-actin-binding proteins appear to serve as linkers of the actin cytoskeleton to the plasma membrane cadherin and integrin.

On the other hand, the linkage between the actin cytoskeleton and the plasma membrane is also important for neuron-specific events, such as growth cone pathfinding and subsequent formation and maintenance of synaptic junction (Neuron 1:761–772, 1988; Science 242:708–715, 1988; Curr. Opin. Neurobiol. 4:43–48, 1994; Curr. Opin. Neurobiol. 4:640–647, 1994; Cell 83:171–176, 1995). However, it remains to be clarified which molecules link the actin cytoskeleton to the plasma membrane in these neuron-specific events.

To address this issue, the inventors of the present patent application have isolated several novel F-actin-binding proteins from rat brain and analyzed the structure of proteins particularly specific to neural tissue and concentrated at synapse, from which an application for a patent has already been filed (Japanese Patent Application No. 9-92615). The protein of the prior invention (hereinafter, referred to as "neurabin" according to the inventor's name) has one F-actin-binding domain and one PDZ domain. The PDZ domain has been found in a variety of proteins, some of which are localized at cell-to-cell junctions, such as PSD-95/SAP90 at synaptic junction (Neuron 9:929–942, 1992; J. Biol. Chem. 268:4580–4583, 1993), Dlg at septate junction (Cell 66:451–464, 1991), ZO-1 and ZO-2 at tight junction (J. Cell Biol. 193:755–766, 1986; Proc. Natl. Acad. Sci. U.S.A. 88:3460–3464, 1991; J. Cell Biol. 121:491–502, 1993; J. Cell Biol. 123:1049–1053, 1993; Proc. Natl. Acad. Sci. U.S.A. 90:7834–7838, 1993; J. Cell Biol. 124:949–961, 1994). In addition, recent studies have revealed that the PDZ domain binds to unique C-terminal motifs of target proteins (Trends Biochem. Sci. 21:455–458, 1996), which are found in a large number of transmembrane proteins, such as N-methyl-D-aspartate receptor and Shaker-type $K^+$ channel (Nature 378:85–88, 1995; Science 259:1737–1740, 1995; J. Neurosci. 16:2157–2163, 1996).

From the various findings described above, it is likely that neurabin, the protein of the prior invention found by the present inventors, serve as a linker of the actin cytoskeleton to a transmembrane protein(s) at synapse.

However, the whole molecular basis for the cell-to-cell adhesion has not yet been clarified, and it is necessary for such clarification to identify further actin filament-binding proteins. In addition, there is a possibility that these proteins leads to clarification of, for example, the mechanisms of infiltration and metastasis of carcinoma, and it is expected that these application allow for the development of diagnostic methods for malignancy of carcinoma, therapeutic methods thereof or agents for carcinoma and the like.

The present invention has been completed under such circumstance. An object of the present invention is to provide a novel actin filament-binding protein contributing to the cell-to-cell adhesion, and simultaneously clarifying its structure (amino acid sequence) and its properties.

Another object of the present invention is to provide a material for genetic engineering manipulation of the actin filament-binding protein.

SUMMARY OF THE INVENTION

In order to satisfy the above described objects, the present application provides an actin filament-binding protein 1-Afadin having the amino acid sequence of SEQ ID NO: 1.

Also, the present invention provides an animal protein having an amino acid sequence substantially the same as that of SEQ ID NO: 1.

Further, the present invention provides a cDNA encoding the amino acid sequence of SEQ ID NO: 1 or an amino acid sequence substantially the same as that of SEQ ID NO: 1, and a genomic DNA sequence to which the cDNA or a partial sequence thereof is hybridized.

Still further, the present invention provides an antibody prepared using the actin filament-binding protein 1-Afadin as an immunogen.

BRIEF DESCRIPTION OF THE DRAWINGS

The file of this patent contains at least one drawing executed in color.

DESCRIPTION OF THE PREFERRED EMBODIMENTS

Figure 1:
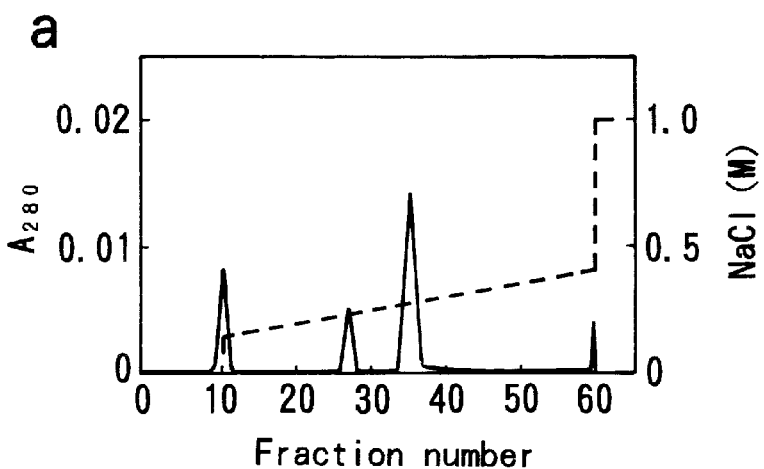
FIG. 1 shows the results of Mono Q column chromatography: (a) absorption at 280 nm ($A_{280}$); (b) blot overlay with $^{125}$I-labeled F-actin; and (c) protein staining after SDS-PAGE.
Figure 1:
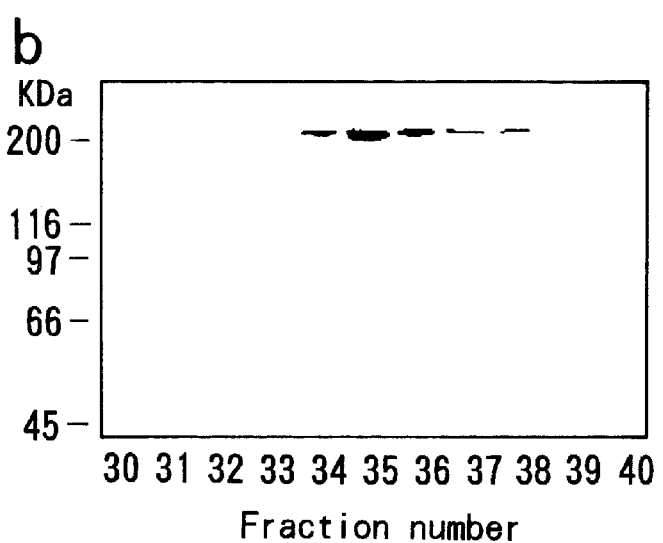
Figure 1:
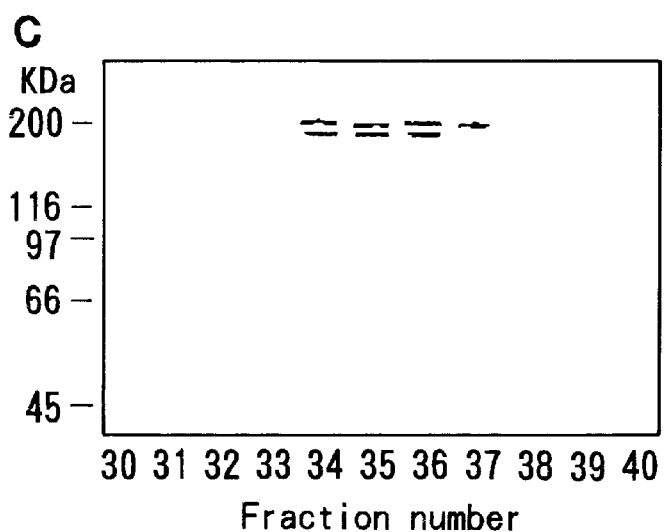

The actin filament-binding protein 1-Afadin of the present invention is a protein having the amino acid sequence of SEQ ID NO: 1. The protein includes peptide fragments (of 5 or more amino acid residues) containing any partial amino acid sequence in the amino acid sequence of SEQ ID NO: 1. These peptide fragments can be used as an antigen for producing antibodies. In addition, the protein of the present invention includes fused proteins with any other proteins (for example, fluorescent proteins and the like).

The protein of the present invention can be isolated from human organs, cell lines and so on by the known methods. When the protein is used in the form of a peptide, it can also be prepared by the chemical synthesis based on the amino acid sequence provided by the present invention. Alternatively, it can be obtained by producing in vitro using the recombinant DNA techniques with a cDNA fragment provided by the present invention. For example, when the protein is obtained by recombinant DNA techniques, a cDNA fragment can be inserted into an appropriate expression vector, and the protein of the present invention can be mass-expressed from the cells (such as *Escherichia coli, Bacillus subtilis*, yeast, animal cell and the like) which are transformed with the recombinant vector. Specifically, for example, when the protein is expressed in a microorganism such as *E. coli*, an expression vector is prepared by inserting the cDNA of the present invention into an expression vector having an origin which can be replicated in the microorganism, a promoter, a ribosome-binding site, cDNA cloning site, and a terminator. Host cells are transformed with the expression vector, and then the obtained transformant is cultured so that the protein encoded by the cDNA is mass-produced in the microorganism. Alternatively, the protein can be expressed as a fusion protein with another protein. The simple protein encoded by the cDNA can be obtained by incision of the obtained fusion protein with an appropriate protease. On the other hand, when the protein of the present invention is desired to be expressed in animal cells, the cDNA fragment is inserted into an expression vector for animal cell having a promoter for animal cell, a splicing region, a poly(A)-addition site, and then the vector is introduced so that the protein of the present invention is expressed in the animal cells.

The genomic DNA sequence of the present invention is a gene of human or other animals encoding the above protein. For example, it can be isolated from any genome library using a cDNA of the present invention or a partial sequence thereof as a probe.

The cDNA of the present invention is a DNA fragment encoding the protein having the amino acid sequence of SEQ ID NO: 1. For example, a clone of the cDNA of the present invention can easily be obtained by screening a cDNA library prepared from rat by means of an oligonucleotide probe synthesized on the basis of the base sequence of the fragment. Alternatively, using the oligonucleotide as a primer, the desired cDNA can be synthesized by the polymerase chain reaction (PCR) method. Generally, the polymorphism is frequently observed in animal gene by the individual variation. Therefore, it is to be appreciated that any cDNA having a single or plural addition, deletion and/or substitution of a nucleotide by other nucleotide is included in the present invention. Similarly, any protein having a single or plural addition, deletion and/or substitution of amino acid by other amino acid is included within the scope of the present invention, insofar as it has an activity of the protein having the amino acid sequence of SEQ ID NO: 1.

The partial amino acid sequence of the cDNA of the present invention is a continuous sequence of 10 bps or more. DNA fragments (sense strand and antisense strand) comprising the continuous sequence are also included in the scope of the present invention. These DNA fragments can be used as probes for gene diagnosis.

In addition, the antibody of the present invention can be obtained as a polyclonal antibody or a monoclonal antibody by the known methods using the above-described protein itself or a partial peptide as the antigen.

EXAMPLES

The present invention will now be described in more detail and specific by means of Examples, which should not be construed as a limitation upon the scope of the present invention.

Example 1

Identification and purification of actin-binding protein 1-Afadin

Growth cons were isolated from rat fetal brain and subjected to the blot overlay method (Cell Motil. Cytoskeleton, 18:164–179, 1991) with $^{125}$I-labeled F-actin to identify a band corresponding to a molecular weight of 205 kDa (p205). The result of the competition experiments showed that the protein bound specifically to F-actin but did not bind to G-actin (actin monomer), indicating that the protein was an F-actin-binding protein.

Next, the soluble fraction of rat fetal brain was subjected to SDS-PAGE and the protein band with a molecular weight (Mr) of 205 kDa was purified by column chromatographies such as Q-Sepharose, phenyl-5PW, hydroxyapatite, Mono Q. The result of the final Mono Q column chromatography is shown in FIG. 1. In FIG. 1, (a) shows an absorption in 280 nm, (b) shows the result of blot overlay with $^{125}$I-labeled F-actin and (c) shows the protein bands stained with Coomassie brilliant blue. As shown in FIG. 1 (c), the purified protein finally gave bands with a Mr of about 205 kDa (p205) and of about 190 kDa (p190). Then, the two purified proteins were excised form the polyacrylamide gel, subjected to limited digestion with a protease (lysyl endopeptidase) and subjected to peptide mapping. Five peptides common to the two proteins were isolated and partial amino acid sequences thereof were separately determined. As the result of homology search using a sequence data base, it was confirmed that the five peptide peaks were significantly homologous to those of human AF-6 protein. On the other hand, the amino acid sequence of the two peptide peaks specific to p205 were not found in current protein data base. The results suggested that p205 and p190 were human AF-6 protein-related rat proteins, and p190 was a splicing variant, a homologue, or a degradative product of p205. In addition, since the p205 was localized in AJ site, the protein was named a large splicing variant of AF-6 protein localized at adherens junction: 1-Afadin" (hereinafter, the protein of the present invention is referred to as 1-Afadin or p205).

Example 2

Cloning of a gene for the actin filament-binding protein 1-Afadin

Figure 2:
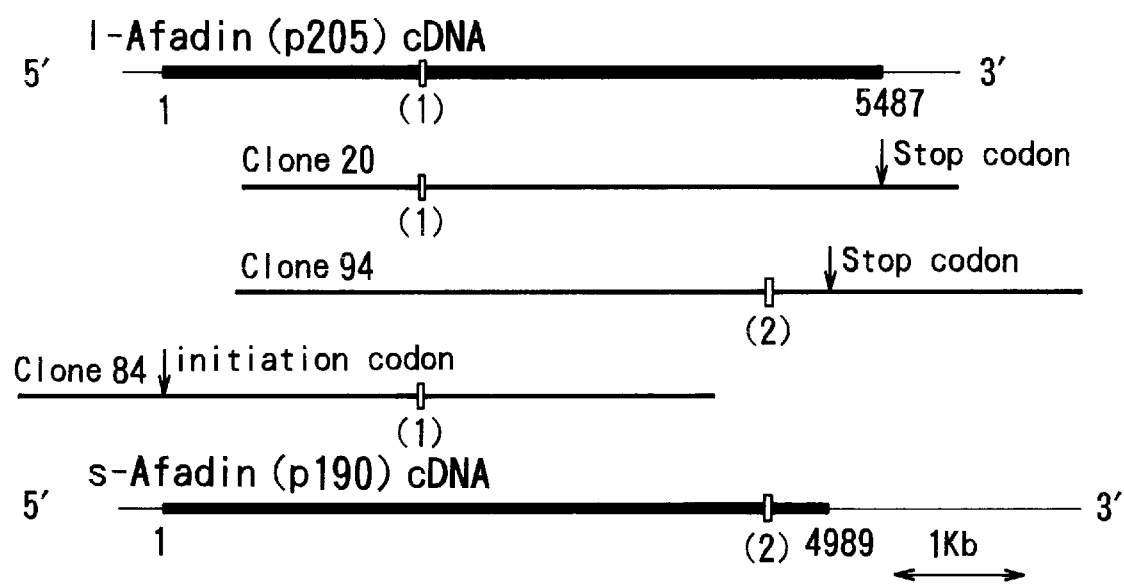
FIG. 2 is a schematic drawing of cDNA of 1-Afadin (p205) and that of s-Afadin (p190).

Based on the partial amino acid sequences of the 205 kDa protein 1-Afadin obtained in Example 1, 7 oligonucleotide probes were prepared and used for screening of rat brain cDNA library. As the result, several overlapping clones as shown in FIG. 2 were obtained. The result of sequencing indicated that, among these clones, clone 20 contained about a coding region with 4.9 kbp and an amino acid sequence estimated from this coding region included the whole peptides of p205. In addition, 2 peptides specific to p205 were localized in the C-terminal. Clone 94 contained a coding region of about 4.5 kbp encoding p190. However, these clones 20 and 94 did not contain the initiation codon, which was contained in clone 84. Therefore, the full-length cDNA for p205 was constructed from the clone 84 and 20, and the full-length cDNA for p190 from the clones 84 and 94.

On the other hand, the FISH analysis (Cytogenet. Cell Genet. 61:282–285,1992; Electrophoresis 16:261–272, 1995) using the clones 20, 84 and 94 as probes indicated that these cDNAs were localized on rat chromosome 1q12.2.

Example 3

Expression of F-actin-binding protein 1-Afadin in animal cells

Figure 3:
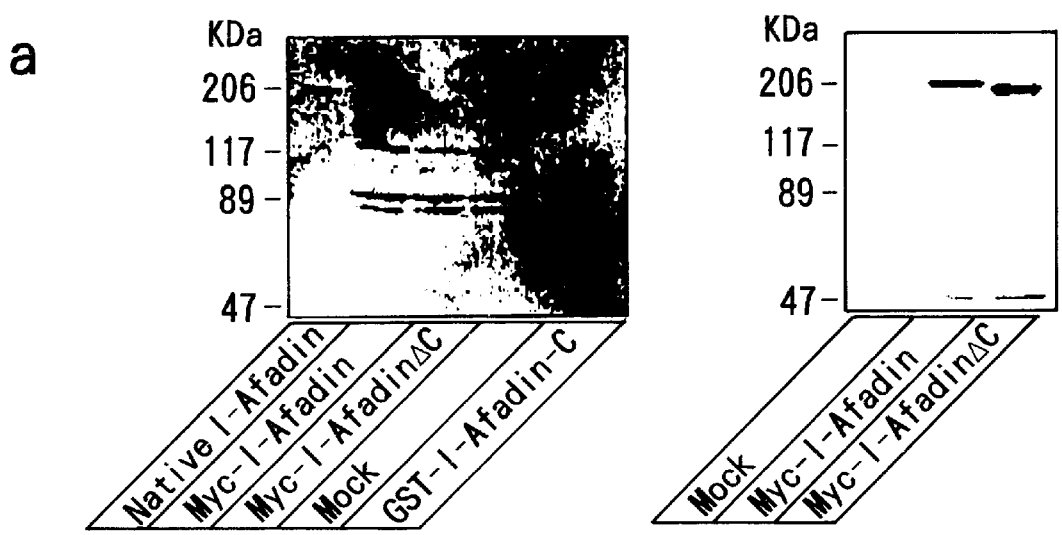
FIG. 3 shows (a) the F-actin-binding activity of various fragments of recombinant 1-Afadin: left is the results of $^{125}$I-labeled F-actin blot overlay; right is the result of Western blot analysis, and (b) a schematic drawings of the structures of 1-Afadin and s-Afadin.
Figure 3:
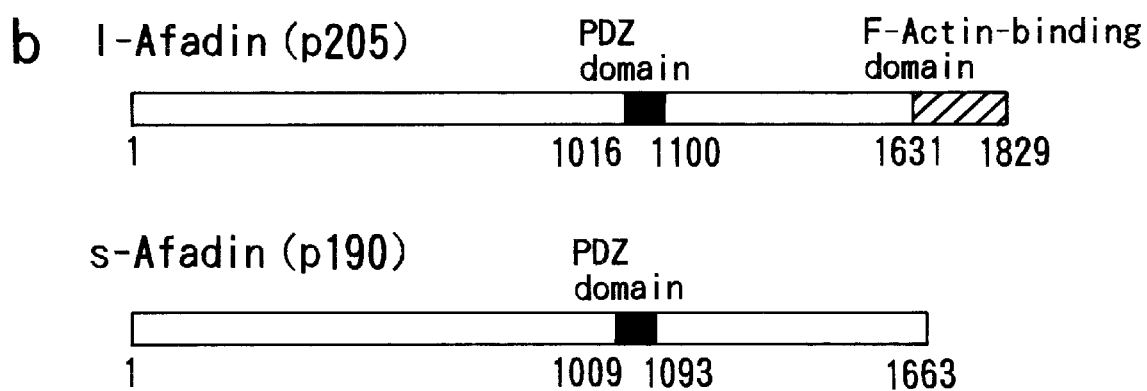

The p205 cDNA prepared in Example 2 was inserted into an expression vector, and transfected into COS7 cells. The cell extract was subjected to the blot overlay with $^{125}$I-labeled F-actin. The recombinant protein (myc-1-adafin) showed the mobility similar to that of native p205 on SDS-PAGE and the binding activity to $^{125}$I-labeled F-actin as shown in FIG. 3(a). On the other hand, the deletion mutant of p205 lacking the C-terminal 156 amino acid did not show the F-actin-binding activity. In contrast, a fusion protein of the C-terminal (199 amino acid residues) of p205 and GTS (glutathione-S-transferase) did show the $^{125}$I-labeled F-actin-binding activity.

From the above results, it was confirmed that the p205 gene encodes a protein of 1,829 amino acids as showed in SEQ ID NO: 1, had an estimated molecular weight of 207,667 and had an F-actin-binding domain on 199 amino acid residues in the C-terminal. Further, it was concluded that the p190 gene encodes a protein lacking about 160 amino acid residues in the C-terminal and was a splicing variant of the p205 gene.

Computer homology search revealed that the amino acid sequence of p190 showed 90% identity over the entire sequence of human AF-6 protein. However, human AF-6 protein and p-190 lacked the C-terminal region of p205. Further, the C-terminal F-actin-binding domain showed no significant homology to any other F-actin-binding protein. Therefore, it was confirmed that, while p190 is likely to be a rat counterpart of human AF-6, p205 is a novel F-actin-binding protein. As shown in FIG. 3(b), both p205 and p190 and one PDZ domein.

Example 4

Preparation of anti-1-Afadin antibody

According to the known methods and using a synthetic peptide corresponding to the amino acid sequence of 1814th-1829th of SEQ ID NO: 1 as an immunogen, a rabbit polyclonal antibody specifically recognizing 1-Afadin was prepared. Also, using a synthetic peptide corresponding to the sequence of 557–592 of SEQ ID NO: 1 as an immunogen, a rabbit polyclonal antibody specifically recognizing both 1-Afadin and S-Afadin was prepared.

EXAMPLE 5

Confirmation of tissues expressing 1-Afadin

Northern blot analysis using a sequence specific to 1-Afadin cDNA as a probe indicated that 1-Afadin was ubiquitously expressed in all the rat tissues examined, including heart, brain, spleen, lung, liver, skeletal muscle, kidney and testis, as shown in FIG. 4(a).

Figure 4:
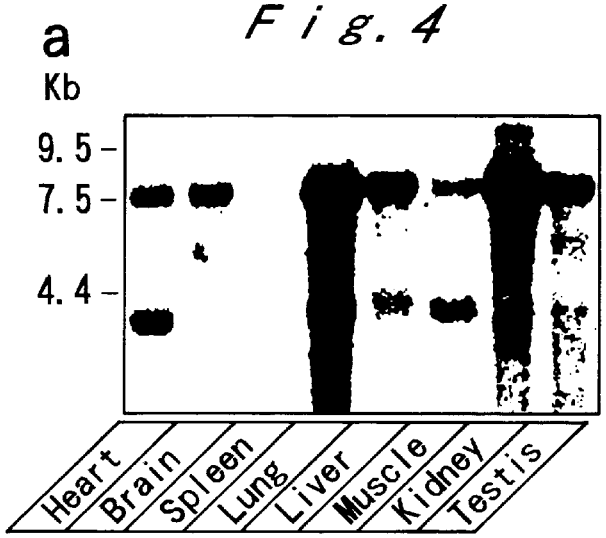
FIG. 4 shows results of analysis of tissue distribution of 1-Afadin: (a) Northern blot analysis, and (b) Western blot analysis with (b1) anti-1-Afadin antibody and (b2) anti-1-Afadin/s-Afadin antibody.
Figure 4:
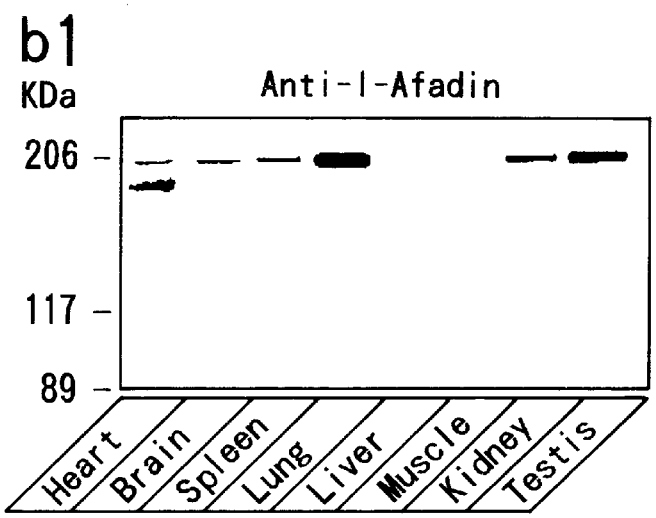
Figure 4:
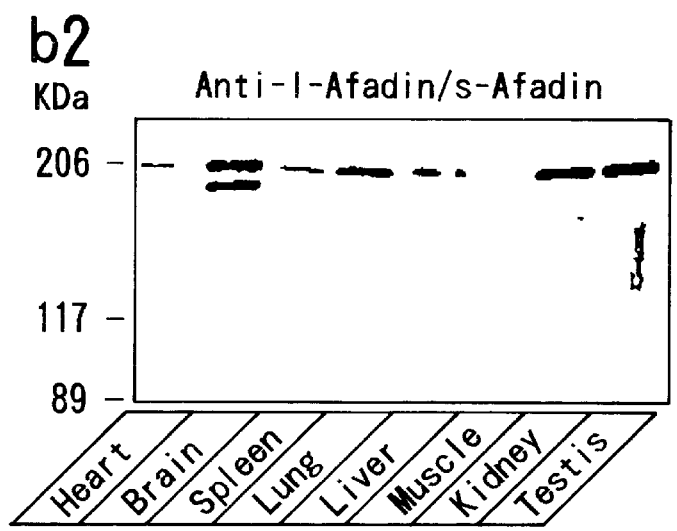

Further, it was confirmed that 1-Afadin was expressed in all the rat tissues from the result of Western blot analysis using the anti-1-Afadin antibody prepared in Example 4, as shown in FIG. 4 (b1). However, as shown in FIG. 4 (b2), it was confirmed that s-Afadin was expressed in brain alone among the organs by the result of Western blot analysis using the antibody recognizing both 1-Afadin and s-Afadin.

From the above results, it was confirmed that, while s-Afadin was expressed only in brain, 1-Afadin of the present invention was ubiquitoulsy expressed.

Example 6

Biochemical characteristics of 1-Afadin

Figure 5:
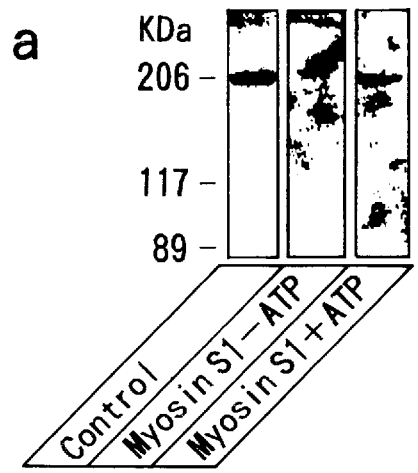
FIG. 5 shows the biochemical properties of 1-Afadin including (a) the inhibition of F-actin binding activity of 1-Afadin by myosin S1, (b) the increase in viscosity of F-actin by 1-Afadin, and (c) the binding of His6-1-Afadin-C to F-actin.
Figure 5:
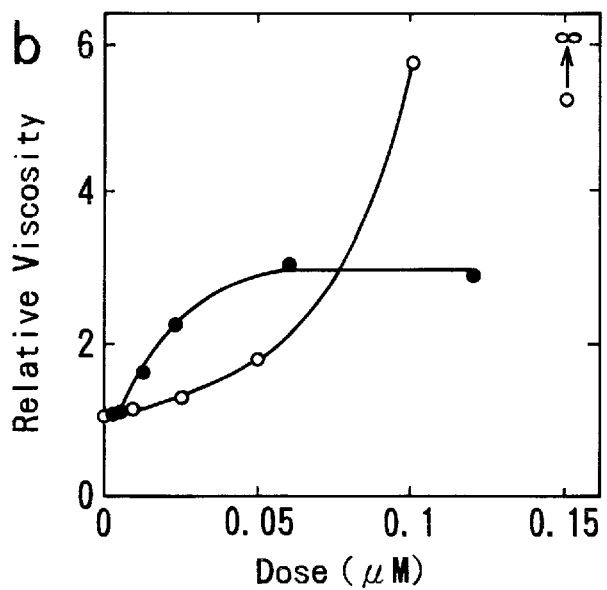
Figure 5:
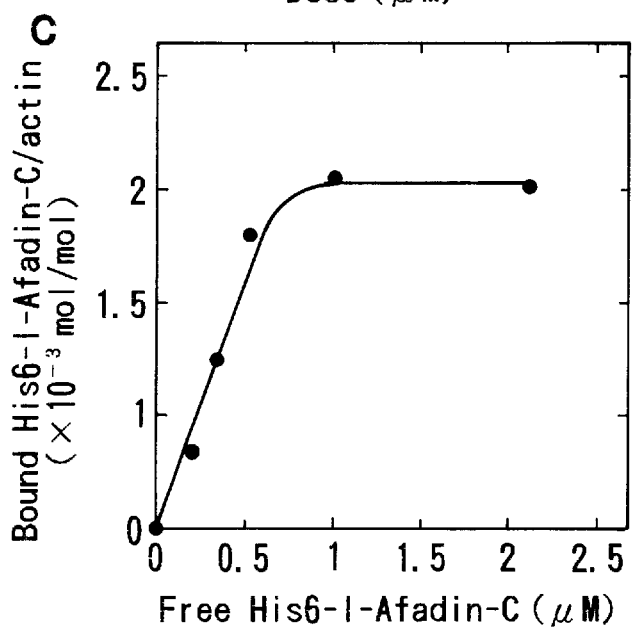

The blot overlay study for the actin-binding ability of the 205 kDa protein (1-Afadin) obtained in Example 1 revealed that the binding of 1-Afadin to F-actin was specifically inhibited by myosin S1 (FIG. 5(a)), but the inhibition disappeared by the addition of Mg ATP. Since myosin S1 is a protein which is confirmed as binding to the lateral of F-actin (Science 261:58–65, 1993; Nature 364:171–174, 1993) and Mg ATP is known to dissociate F-actin-myosin complex (Biochemistry 14:2207–2214, 1975), it was confirmed that 1-Afadin binds along the side of F-actin.

Next, a change in viscosity of F-actin by 1-Afadin was studied by the falling ball method (Methods Enzymol. 85:211–233, 1982; J. Biol. Chem. 271:31775–31778, 1996). As the result, 1-Afadin increased dose-dependently the viscosity of F-actin, up to a viscosity of about 3 times in the maximum, as shown in FIG. 5(b).

In addition, the result (FIG. 5(c)) of calculation of the stoichiometry indicated that His6-1-Afadin-C in a rate of 1 molecule per about 500 molecules of G-actin and that the Kd value was in a order of $10^{-7}$ M (moler).

Further, the effect of 1-Afadin on F-actin was examined using pyrene-conjugated actin. It was found that 1-Afadin does not affect the actin polymerization.

Example 7

Localization of 1-Afadin

Using the anti-1-Afadin antibody, frozen slices of various mouse and rat tissues were observed with confocal microscopy to identify the localization of 1-Afadin.

Figure 6:
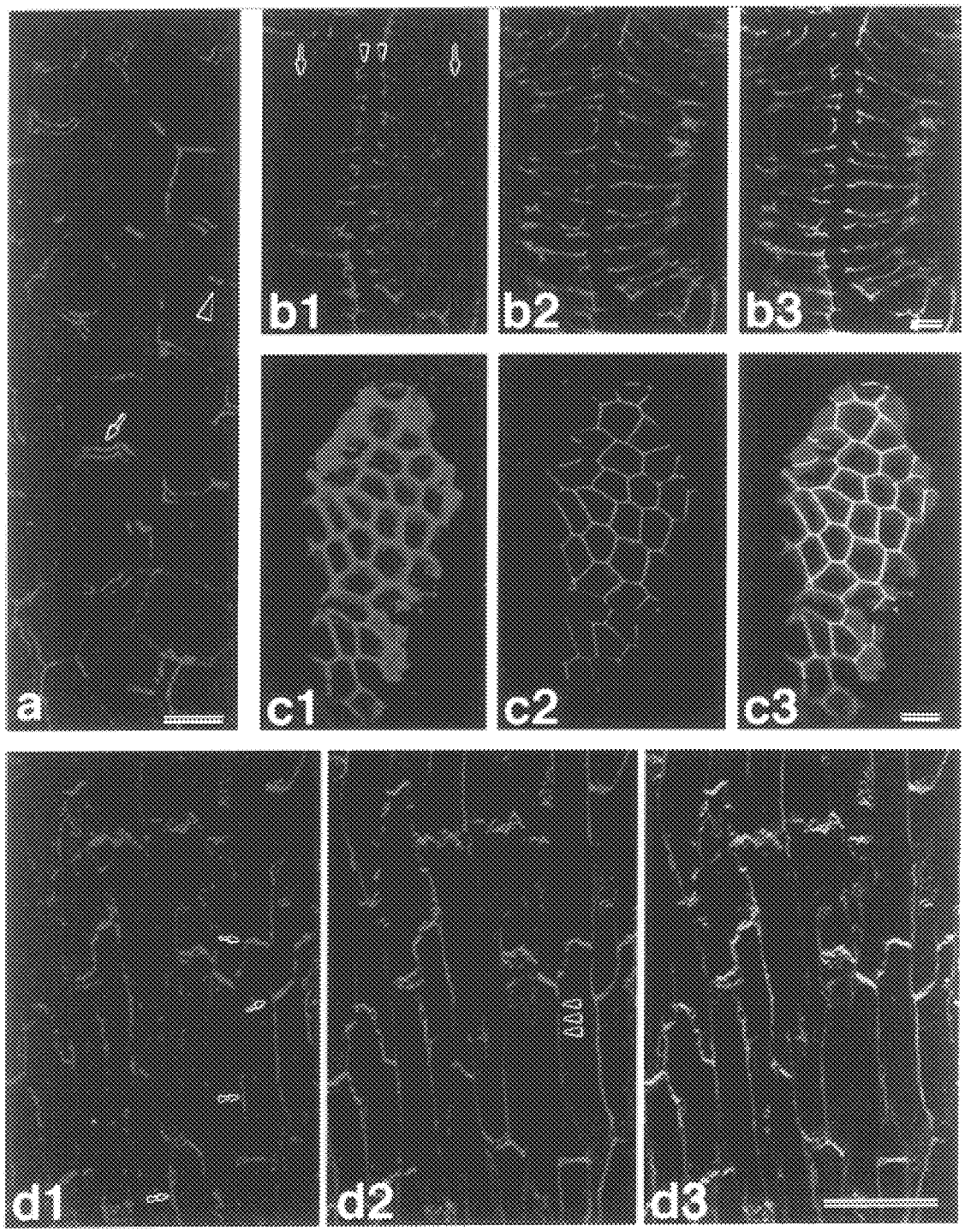
FIG. 6 shows photographs indicating the localization of 1-Afadin, E-cadherin and vinculin in various rat and mouse tissues.
Figure 7:
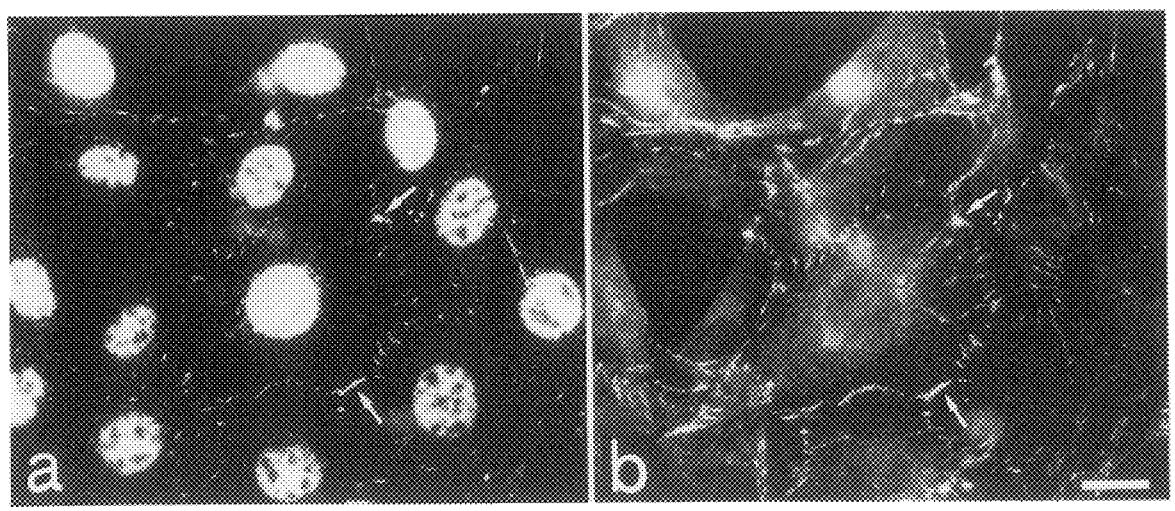
FIG. 7 shows photographs indicating the localization of 1-Afadin and ZO-1 in EL cells.

In liver, 1-Afadin was localized in a belt-like junctional complex region along the bile canaliculi (FIG. 6(a)). In the small intestine, which was doubly stained with the anti-E-cadherin monoclonal antibody, 1-Afadin was detected in a junctional complex region of intestinal absorptive epithelium together with E-cadherin, but was more concentrated in the region than E-cadherin was (FIG. 6(b1)–(b3) and (c1)–(c3)). Heart was doubly stained with the anti-vinculin monoclonal antibody. Vinculin has been known as markers for not only cell-to-cell AJ but also for cell-to-matrix AJ (Cell 18:193–205, 1979; Biochem. Biophys. Acta 737:305–341, 1983). As the result, 1-Afadin was colocalized with vinculin at intercalated disc (FIG. 6(d1)–(d3)). However, while vinculin was also periodically located along the lateral border of cardiac muscle cells, 1-Afadin was not detected in this region. In addition, when cultured EL cells expressing E-cadherin (Nature 329:341–343, 1987) were doubly stained with the anti-ZO-1 antibody, the localization of 1-Afadin was similar to that of ZO-1 (FIG. 7(a) and (b)). Since ZO-1 is known to be concentrated at cadherin-based spot-like cell-to-cell AJ in fibroblast (J. Cell Biol. 115:1149–1462, 1991; J. Cell Biol. 121:491–502, 1993), it was suggested that 1-Afadin is also localized at cadherin-based cell-to-cell AJ.

Figure 8:
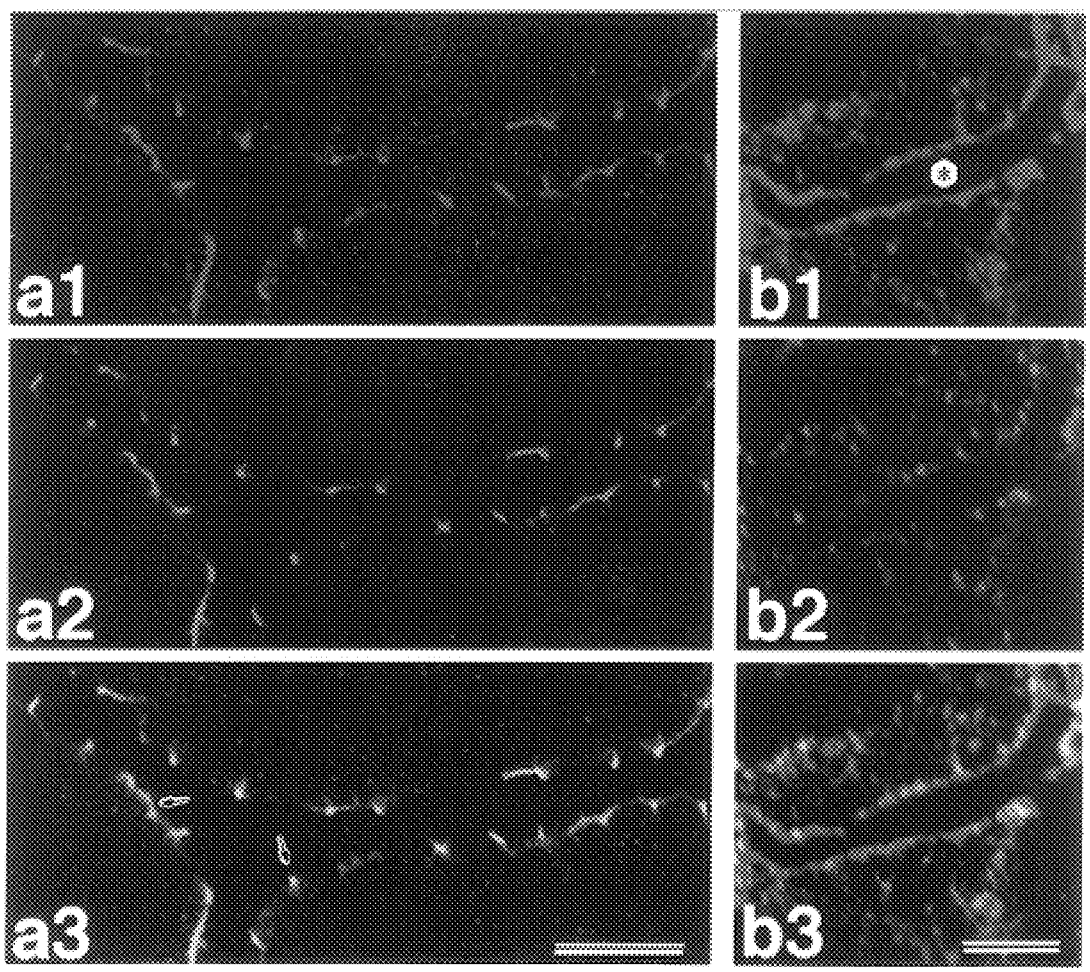
FIG. 8 shows photographs indicating the different localizations of 1-Afadin, ZO-1 and desmoplakin.

Further, in order to examine the precise localization of 1-Afadin, a frozen sections of small intestine were doubly stained with the anti-ZO-1 monoclonal antibody and the anti-1-Afadin antibody. In addition, liver bile canaliculi were doubly stained with the anti-desmoplakin monoclonal antibody and the anti-1-Afadin antibody. ZO-1 was known to be a marker for tight junction in intestinal absorptive epithelium (J. Cell Biol. 103:755–766, 1986; J. Cell Biol. 121:491–502, 1993) and desmoplakin was known to be a marker for desmosome (J. Cell Biol. 63:515–523, 1974; Eur. J. Cell Biol. 32:117–130, 1983; J. Mol. Biol. 163:647–671, 1983; EMBO J. 6:885–889, 1987). The results showed that, in the absorptive epithelia of small intestine, 1-Afadin was localized slightly more at the basal side than ZO-1 (FIG. 8(a1)–(a3)). In the bile duct, the localization of 1-Afadin did not coincide with that of desmoplakin (FIG. 8(b1)–(b3)).

Figure 9:
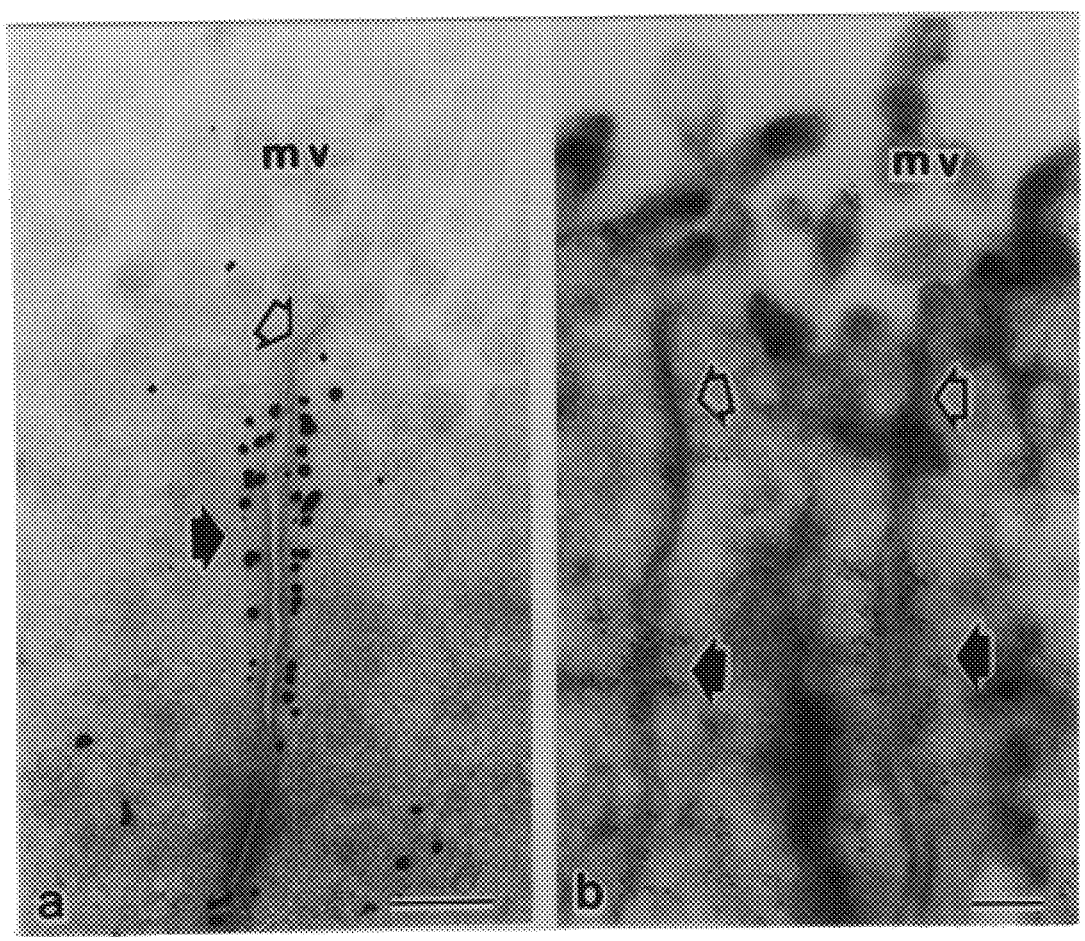
FIG. 9 shows photographs indicating the localization of 1-Afadin in rat small intestine.

These results indicate that 1-Afadin is localized at cell-to-cell AJ rather than at tight junction and desmosome. Further, according to immunoelectron microscopy, it was observed that 1-Afadin was localized in cell-to-cell AJ of absorptive epithelia of small intestine (FIG. 9(a) and (b)).

Accordingly, it was confirmed that 1-Afadin of the present invention is a novel protein uniting the actin cytoskeleton and cell-to-cell AJ.

As described above in detail, the present invention provides a novel actin filament-binding protein 1-Afadin localized at the cadherin cell-to-cell adherens junction, the antibody specifically detecting 1-Afadin, and the genetic materials for industrially utilizing 1-Afadin.

What is claimed is:

1. An isolated actin-binding protein 1-Afadin having the amino acid sequence as set forth in SEQ ID NO: 1.

2. An isolated cDNA encoding the amino acid sequence as set forth in SEQ ID NO: 1.

3. An isolated antibody prepared using an amino acid sequence unique to the actin binding protein 1-Afadin of claim 1 as an immunogen.

4. An isolated antibody which only specifically binds to the actin-binding protein 1-Afadin of claim 1.

* * * * *